United States Patent [19]

Phillipps et al.

[11] Patent Number: 4,900,737
[45] Date of Patent: Feb. 13, 1990

[54] ISOQUINOLINE DERIVATIVES

[75] Inventors: Gordon H. Phillipps, Wembley; Esme J. Bailey, Richmond; Michael G. Lester, Rickmansworth, all of United Kingdom

[73] Assignee: Glaxo Group Limited, London, England

[21] Appl. No.: 250,216

[22] Filed: Sep. 28, 1988

Related U.S. Application Data

[63] Continuation of Ser. No. 868,071, May 29, 1986, abandoned.

[30] Foreign Application Priority Data

May 29, 1985 [GB] United Kingdom ............... 8513460

[51] Int. Cl.$^4$ ................. A61K 31/47; C07D 471/04; C07D 471/14
[52] U.S. Cl. ................. 514/279; 514/283; 546/41; 546/42
[58] Field of Search ............. 546/41, 42; 514/279, 514/283, 214, 222, 236, 253; 544/125, 60, 361

[56] References Cited

U.S. PATENT DOCUMENTS

| | | | |
|---|---|---|---|
| 3,894,029 | 7/1975 | Winterfeldt et al. | 546/48 |
| 3,903,276 | 9/1975 | Nudelman et al. | 514/221 |
| 4,029,659 | 6/1977 | Hannart | 546/48 X |
| 4,301,285 | 11/1981 | Stein | 544/138 |
| 4,548,819 | 10/1985 | De Clercq et al. | 514/261 |
| 4,835,158 | 5/1989 | Phillips et al. | 514/279 |

FOREIGN PATENT DOCUMENTS

| | | | |
|---|---|---|---|
| 0161102 | 11/1985 | European Pat. Off. | 514/283 |
| 2129799 | 5/1984 | United Kingdom | 546/42 |

*Primary Examiner*—Mukund J. Shah
*Assistant Examiner*—Diana G. Rivers
*Attorney, Agent, or Firm*—Bacon & Thomas

[57] ABSTRACT

Compounds of formula (I)

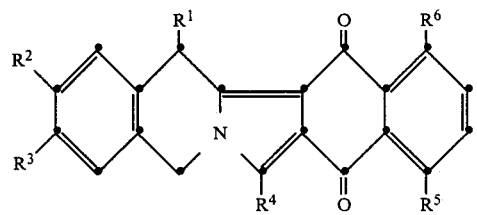

(wherein
$R^1$ is a hydrogen atom or a methyl group;
$R^2$ is a hydrogen atom or a hydroxyl, $C_{1-4}$ alkoxy or $C_{2-4}$ alkanoyloxy group;
$R^3$ is a hydrogen atom, or (when $R^2$ is other than a hydrogen atom) optionally a hydroxyl, $C_{1-4}$ alkoxy or $C_{2-4}$ alkanoyloxy group, or $R^2$ and $R^3$ together are a methylenedioxy group;
$R^4$ is a hydrogen or halogen atom or a methyl group;
$R^5$ and $R^6$ is each a hydrogen atom or a group —O—COCH$_2$NR$^7$R$^8$ [where $R^7$ and $R^8$, which may be the same or different, each is a hydrogen atom or a $C_{3-7}$ cycloalkyl group or a straight or branched $C_{1-4}$ alkyl group optionally substituted by a hydroxyl group, or —NR$^7$R$^8$ forms a saturated heterocyclic amino group which has 5–7 ring members and optionally contains in the ring an oxygen or sulphur atom or a group —NH— or —N(R) where R is a $C_{1-4}$ alkyl group optionally substituted by a hydroxyl group] with the proviso that when one of $R^5$ and $R^6$ is a hydrogen atom, the other is a group —OCOCH$_2$NR$^7$R$^8$) may be prepared by amination of a corresponding compound where $R^5$ and/or $R^6$ is a group —OCOCH$_2$L wherein L is a displaceable leaving group. The compounds of formula (I) and their physiologically acceptable salts exhibit interesting cancer combatting properties.

9 Claims, No Drawings

ISOQUINOLINE DERIVATIVES

This application is a continuation of application Ser. No. 868,071, filed May 29, 1986, now abandoned.

This invention relates to new isoquinoline derivatives, to processes for their preparation, to pharmaceutical preparations containing them, and to their use in medicine.

Isoquinoline compounds have been reported in for example EP-A-108620 and EP-A-161102 as exhibiting anti-cancer activity. We have now found certain novel isoquinoline compounds to possess particularly interesting pharmacological properties, in particular anti-cancer activity. Compounds according to the invention also have especially useful physico-chemical properties which make them very suitable for pharmaceutical formulation.

The invention thus provides compounds of the general formula

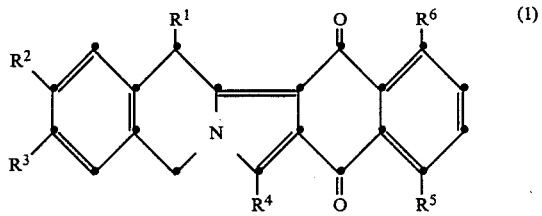

wherein
$R^1$ is a hydrogen atom or a methyl group;
$R^2$ is a hydrogen atom or a hydroxyl, $C_{1-4}$ alkoxy or $C_{2-4}$ alkanoyloxy group;
$R^3$ is a hydrogen atom, or (when $R^2$ is other than a hydrogen atom) optionally a hydroxyl, $C_{1-4}$ alkoxy or $C_{2-4}$ alkanoyloxy group, or $R^2$ and $R^3$ together are a methylenedioxy group;
$R^4$ is a hydrogen or halogen atom or a methyl group;
$R^5$ and $R^6$ is each a hydrogen atom or a group —O—COCH$_2$NR$^7$R$^8$ [where $R^7$ and $R^8$, which may be the same or different, each is a hydrogen atom or a $C_{3-7}$ cycloalkyl group or a straight or branched $C_{1-4}$ alkyl group optionally substituted by a hydroxyl group, or —NR$^7$R$^8$ forms a saturated heterocyclic amino group which has 5-7 ring members and optionally contains in the ring an oxygen or sulphur atom or a group —NH— or —N(R)— where R is a $C_{1-4}$ alkyl group optionally substituted by a hydroxyl group] with the proviso that when one of $R^5$ and $R^6$ is a hydrogen atom, the other is a group OCOCH$_2$NR$^7$R$^8$;
and salts, especially physiologically acceptable salts, thereof.

Compounds of formula (1) may exist as stereoisomers, and the invention is to be understood to include all such isomers of compounds of formula (1), including mixtures thereof.

The compounds of formula (1) may form salts with acids. It will be appreciated that, for pharmaceutical use, these salts will be physiologically acceptable, but other salts may find use, for example in the preparation of compounds of formula (1) as well as physiologically acceptable salts thereof.

Suitable physiologically acceptable salts of the compounds of general formula (1) are acid addition salts derived from inorganic and organic acids. Such salts include for example the hydrochlorides, hydrobromides, sulphates, phosphates, maleates, tartrates, citrates, benzoates, acetates, fumarates and succinates of the compounds of formula (1). Hydrochloride salts are particularly important. References hereinafter to compounds of formula (1) are, unless the context demands otherwise, to the compounds themselves and to their physiologically acceptable salts.

In general formula (1), the group $R^1$ is preferably a methyl group.

The group $R^2$ may be for example a hydrogen atom or a hydroxyl, methoxy, ethoxy or acetyloxy group, and is preferably a hydrogen atom.

When the group $R^3$ is a $C_{1-4}$ alkoxy or $C_{2-4}$ alkanoyloxy group it may be for example a methoxy, ethoxy or acetyloxy group. $R^3$ is preferably a hydrogen atom.

In one group of compounds of formula (I) $R^2$ is a hydrogen atom or a hydroxyl group, particularly a hydrogen atom, and $R^3$ is a hydrogen atom.

When the group $R^4$ in general formula (1) is a halogen atom it may be a fluorine, chlorine, bromine or iodine atom, in particular a bromine atom.

In general, $R^4$ is preferably a hydrogen atom or a methyl group. In another preference $R^4$ is a bromine atom.

Examples of alkyl groups represented by $R^7$ or $R^8$ in compounds of formula (1) include methyl, ethyl, propyl and butyl, optionally substituted by a hydroxy group, for example 2-hydroxyethyl. When $R^7$ or $R^8$ is a cycloalkyl group it may be for example cyclopropyl.

When —NR$^7$R$^8$ in compounds of formula (1) represents a saturated heterocyclic amino group, this may have 5, 6 or 7 ring members and optionally contains in the ring an oxygen or sulphur atom or a group —NH— or —N(R)— where R may be for example a methyl or ethyl group optionally substituted by a hydroxyl group e.g. 2-hydroxyethyl. Examples of such groups —NR$^7$R$^8$ are pyrrolidino, piperidino, hexamethyleneimino, piperazino, N-methylpiperazino, morpholino or thiomorpholino.

In general, the group $R^5$ or $R^6$ in compounds of formula (1) is preferably a hydrogen atom or a group —O—COCH$_2$NR$^7$R$^8$ where $R^7$ and $R^8$ each represents a straight or branched $C_{1-4}$ alkyl group, particularly an ethyl group.

In particular, the group $R^5$ is preferably a group —O—COCH$_2$NR$^7$R$^8$ where $R^7$ and $R^8$ each represents a straight or branched $C_{1-4}$ alkyl group and is especially a group —OCOCH$_2$N(CH$_3$)$_2$, —OCOCH$_2$N(CH$_2$CH$_3$)$_2$ or —OCOCH$_2$N(CH$_2$CH$_2$CH$_3$)$_2$, particularly —O—COCH$_2$N(CH$_2$CH$_3$)$_2$. The group $R^6$ is preferably a group —OCOCH$_2$N(CH$_3$)$_2$, —OCOCH$_2$N(CH$_2$CH$_3$)$_2$ or —OCOCH$_2$N(CH$_2$CH$_2$CH$_3$)$_2$, or more preferably is a hydrogen atom.

A particularly preferred group of compounds according to the invention has the formula (1a):

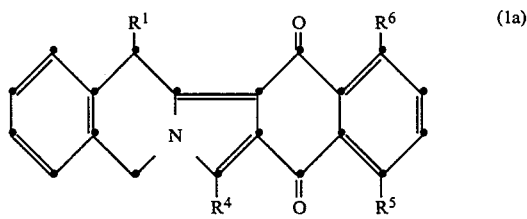

where $R^1$ is a hydrogen atom or a methyl group;

$R^4$ is a hydrogen or halogen atom or a methyl group;

$R^5$ and $R^6$ is each a hydrogen atom or a group —OCOCH$_2$NR$^7$R$^8$ where $R^7$ and $R^8$, which may be the same or different each is a straight or branched $C_{1-4}$ alkyl group; and the salts, especially the physiologically acceptable salts, thereof.

In compounds of formula (1a) $R^1$ is preferably a methyl group.

$R^4$ is preferably a bromine atom or a methyl group, or, in particular, a hydrogen atom.

$R^5$ is preferably a group —OCOCH$_2$NR$^7$R$^8$ where $R^7$ and $R^8$ each represents a straight or branched $C_{1-4}$ alkyl group, especially a methyl, propyl or, in particular, an ethyl group. Particularly preferred $R^5$ groups are —OCOCH$_2$N(CH$_3$)$_2$, —OCOCH$_2$N(CH$_2$CH$_2$CH$_3$)$_2$, and especially —OCOCH$_2$N(CH$_2$CH$_3$)$_2$.

$R^6$ is preferably a hydrogen atom.

A particularly important compound of formula (1) is (diethylamino)acetic acid [5,8,13,14-tetrahydro-14-methyl-8,13-dioxobenz[5,6]isoindolo[2,1-b]isoquinolin-9-yl]ester and its physiologically acceptable salts, especially the hydrochlorides thereof.

The compounds of formula (1) possess anticancer activity, particularly against tumours such as sarcomas, carcinomas and hepatomas.

Thus, when a compound of formula (1) is administered intraperitoneally, intravenously or orally to mice with a subcutaneous tumour arising from an implant of S180 cells, subsequent examination has shown that tumour growth has been significantly reduced and in some cases total regression of the tumour has occurred. Activity against L1210 (Mouse lymphocytic leukaemia, grown ascitally) has also been shown.

According to a further aspect of the present invention we therefore provide a compound of formula (1) for use in the treatment of the human or non-human animal body to combat cancer, particularly tumours, therein.

According to a yet further aspect of the present invention we provide the use of a compound of formula (1) for the treatment of the human or non-human animal body to combat cancer, particularly tumours, therein.

According to a still further aspect of the present invention we provide the use of a compound of formula (1) for the manufacture of a therapeutic agent for the treatment of the human or non-human animal body to combat cancer, particularly tumours, therein.

According to a still further aspect of the present invention we provide a method of treatment of the human or non-human animal body to combat cancers, particularly tumours, therein, which method comprises administering to the said body an effective amount of a compound of formula (1).

The compounds of formula (1) advantageously have good water solubility which make them very suitable for pharmaceutical formulation.

In a further feature of the present invention we provide a pharmaceutical composition comprising as active ingredient a compound of formula (1) together with one or more pharmaceutical carriers or excipients.

For pharmaceutical administration a compound of general formula (1) may be incorporated into conventional preparations in either solid or liquid form.

The compositions may, for example, be presented in a form suitable for oral, rectal, topical or, more preferably, parenteral administration. Suitable forms include, for example, tablets, capsules, granules, suppositories, creams, ointments and lotions and more particularly suspensions and/or solutions for injection or infusion.

The active ingredient may be incorporated in excipients customarily employed in pharmaceutical compositions such as, for example, talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of the compound of formula (1). Suitable dosage units for adults contain from 25 to 1000 mg of the compound of formula (1).

The dosage, which may be varied according to the particular patient to be treated and complaint concerned, may, for example, be from 0.05 to 2.5 g e.g. 0.1 to 1 g in a day in adults.

The compounds useful according to the invention may be prepared by a number of process, described in the following, wherein the various groups and symbols are as defined for formula (1) unless otherwise specified. In these processes, hydroxyl groups, where present, may need to be in a protected form and the final step in a process may thus be the removal of a protecting group. The protecting group may be any suitable hydroxyl protecting group for example as described in "Protective Groups in Organic Synthesis" by Theodora W. Greene (Wiley-Interscience, New York 1981) and "Protective Groups in Organic Chemistry" by J. F. W. McOmie (Plenum Press, London, 1973) and may be for example a silyl group, e.g. t-butyldimethylsilyl. Standard protection and deprotection procedures may be used, for example those extensively described in the aforementioned textbooks of Greene and McOmie. Thus for example protection with a silyl group may be achieved by reaction with a silyl halide in the presence of a base. Subsequent deprotection may be achieved using fluoride ions e.g. from a tetraalkylammonium fluoride such as tetra-n-butylammonium fluoride. Where mixtures of isomers are obtained using the following processes, individual isomers may be separated therefrom by conventional means, for example by chromatography using e.g. silica gel.

A compound of formula (1) in which $R^4$ is a hydrogen atom or a methyl group may be prepared by reaction of a compound of formula (2)

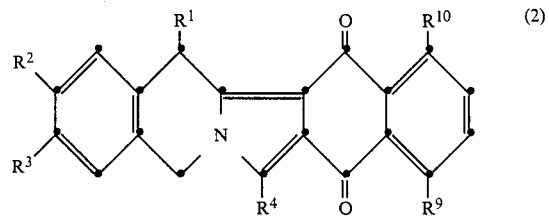

[where $R^4$ is a hydrogen atom or a methyl group; one of $R^9$ and $R^{10}$ is a group —OCOCH$_2$L (in which L is a displaceable leaving group such as a halogen atom, e.g. a chlorine, bromine or iodine atom, or a hydrocarbylsulphonyloxy group such as methanesulphonyloxy or p-toluenesulphonyloxy) and the other is a hydrogen atom; or both $R^9$ and $R^{10}$ are —OCOCH$_2$L groups] with an amine $R^7R^8$NH followed by removal of any protecting groups where present.

The reaction may be effected in the presence of a suitable solvent, for example acetonitrile or a ketone such as acetone, or a substituted amide e.g. dimethylformamide or dimethylacetamide at a temperature from ambient to the reflux.

The intermediates of formula (2) are novel compounds and form a further aspect of the invention.

The intermediates of formula (2) may be prepared by condensing a quinone of formula (3).

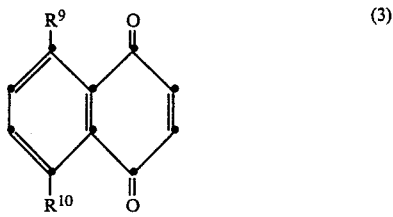

with a compound of formula (4)

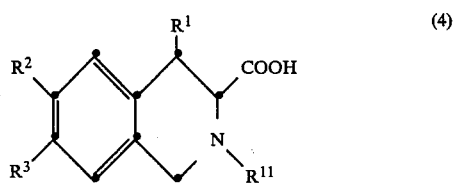

(where $R^{11}$ is a hydrogen atom or a group —CHO or —COCH$_3$) in the presence of an alkanoic acid anhydride, such as acetic anhydride, at an elevated temperature e.g. 100° C.

Compounds of formula (4) are either known compounds, or may be prepared using methods analogous to those used for the preparation of the known compounds.

Intermediates of formula (3) in which $R^9$ and/or $R^{10}$ is a group —OCOCH$_2$L and L is a chlorine atom may be prepared from the corresponding known quinones in which $R^9$ and/or $R^{10}$ is a hydroxyl group, by reaction with chloroacetic anhydride in a solvent such as dioxan in the presence of a base such as 4-dimethylaminopyridine or triethylamine at ambient temperature. The chlorine atoms in these intermediates of formula (4) may be displaced using conventional procedures to prepare intermediates of formula (4) in which L is a leaving group other than a chlorine atom.

Alternatively, compounds of formula (2) in which L is a chlorine atom may be prepared by base catalysed acylation of a corresponding compound in which $R^9$ and/or $R^{10}$ is a hydroxyl group, for example using chloroacetic anhydride in the presence of a base such as sodium hydride in a solvent such as tetrahydrofuran. Displacement of the chlorine atom using conventional procedures the yields other intermediates of formula (2). The starting materials for this reaction may be prepared as described in European Patent Application Publication No. 161102.

Compounds of formula (1) in which $R^4$ is a halogen atom may be prepared by halogenating a corresponding compound in which $R^4$ is a hydrogen atom. Standard halogenation procedures may be used, for example reaction with a N-chloro, N-bromo or N-iodoimide, e.g. N-chloro-, N-bromo- or N-iodosuccinimide in an inert solvent such as dichloromethane at ambient temperature, or by reaction with perchloryl fluoride.

Physiologically acceptable salts of the compounds of general formula (1) may be prepared by reaction of a compound of general formula (1) with an appropriate acid in the presence of a suitable solvent, e.g. dioxan or water The following Examples illustrate the invention. All temperatures are in °C.

INTERMEDIATE EXAMPLES

Intermediate 1

5-Chloroacetoxy-1,4-naphthalenedione

5-Hydroxy-1,4-naphthalenedione (30 g), chloroacetic anhydride (180 g) and 4-dimethylaminopyridine (6 g) in dioxan (750 ml) were stirred at room temperature for 30 minutes then poured onto ice and water (about 4 liters) to give a solid which was collected by filtration, air dried at room temperature (about 2 hours) and then dried under reduced pressure (0.1 mm) at 50° for 17 hours to give the title compound (44 g). A sample was recrystallised (2×) from ethyl acetate-petroleum ether (b.p. 60°-80°) to give the title compound m.p. 125°-127° (d).

Intermediate 2

5-Iodoacetoxy-1,4-naphthalenedione

Intermediate 1 (44 g) and sodium iodide (90 g) in acetone (1500 ml) was stirred for 20 hours at room temperature, then poured onto ice and water (about 6 liters) and allowed to stand at room temperature for 1 hour to yield a solid which was collected by filtration, air dried for 2 hours and then dried under reduced pressure (0.1 mm) at 60° for 18 hours to give the title compound (55.82 g). A sample was purified by chromatography on silica eluting with dichloromethane-ethyl acetate (9:1), followed by recrystallisation from acetone-petroleum ether (b.p. 60°-80°) to yield the title compound m.p. 124°-125°.

Intermediate 3

(Iodo)acetic acid, 5,8,13,14-tetrahydro-8,13-dioxobenz-[5,6]isoindolo[2,1-b]isoquinolin-9-yl ester Intermediate 2 (27.9 g), 2-formyl-1,2,3,4-tetrahydro-3-isoquinolinecarboxylic acid (8.35 g) and acetic anhydride (420 ml) were stirred at 100° for 30 minutes then allowed to cool to room temperature and a green precipitate collected by filtration, washed with acetic anhydride, ethyl acetate and ether, then dried (75°, 0.1 mm) to yield the title compound (12.07 g) m.p. >260° (d).

Intermediate 4

5,8-Dichloroacetoxy-1,4-naphthalenedione 5,8-Dihydroxy-1,4-naphthalenedione (5 g), chloroacetic anhydride (60 g) and dimethylaminopyridine (2 g) in dioxan (250 ml) were stirred at room temperature for 25 hours. The mixture was then poured onto ice and a green solid was collected by filtration, washed and dried (CaCl$_2$, 0.1 mm; then 70° at 0.1 mm for 4 hours) to yield the title compound (11.3 g) $\lambda_{max}$ (ethanol) 247 (E$_1$1378), 316 (E$_1$171) and 399.5 nm (E$_1$183).

Intermediate 5

5,8-Di-iodoacetoxy-1,4-naphthalenedione

Intermediate 4 (11 g) and sodium iodide (44 g) in acetone (550 ml) were stirred for 20 hours at room temperature, the acetone was reduced to low volume and the resulting mixture was poured onto ice to yield a solid which was collected by filtration, washed with water and dried to yield the title compound (13.61 g). A sample was purified by chromatography on silica eluting with dichloromethane then dichloromethane-ethyl acetate (95:1), followed by crystallisation from acetone-petroleum ether (b.p. 60°–80°) to give the title compound m.p. 158°–160°.

Intermediate 6

(Iodo)acetic acid, 5,8,13,14-tetrahydro-8,13-dioxobenz[5,6]isoindolo-[2,1-b]isoquinoline-9,12-diyl ester Intermediate 5 (6.95 g) and 2-formyl-1,2,3,4-tetrahydro-3-isoquinolinecarboxylic acid (1.35 g) in acetic anhydride (34 ml) were stirred at 100° for 20 minutes, and then cooled to room temperature for 1 hour. The resulting precipitate was collected by filtration, washed with acetic anhydride, ethyl acetate and then dried (70°, 0.1 mm) to yield the title compound (3.0 g) $\lambda_{max}$ (ethanol) 241.5 ($E_1^1$ 556), and 385 nm ($E_1^1$ 99).

Intermediate 7

4-Methyltetrahydroisoquinoline-3-carboxylic acid

β-Methyl(dl)phenylalanine hydrochloride (4 g), concentrated hydrochloric acid (20 ml) and formaldehyde (6 ml) were heated with stirring in an oil bath at 100° for 3.5 h and then evaporated to dryness to give a white froth which was dissolved in water (20 ml) and the pH adjusted to 4 with 5M NaOH, under nitrogen. The reaction mixture was stored at 5° for 60 h after which a precipitated white solid was recovered by filtration, washed with a small quantity of water and dried to yield the title compound (1.965 g) m.p. >260° (decomp).

Intermdiate 8

2-Formyl-4-methyltetrahydroisoquinoline-3-carboxylic acid

Acetic anhydride (19 ml) was added to formic acid (19 ml) and the reaction mixture was allowed to stand at room temperature for 2 min. Intermediate 7 (1.9 g) was added and the reaction was stirred at room temperature for 1 h then evaporated to dryness (water pump) and finally dried at 0.1 mm at room temperature overnight. Crystallisation from aqueous methanol gave the title compound (1.19 g) as a white solid.

Intermediate 9

(Iodo)acetic acid, 5,8,13,14-tetrahydro-14-methyl-8,13-dioxobenz-[5,6]isoindolo[2,1-b]isoquinolin-9-yl ester A mixture of Intermediate 2 (6.8 g) and Intermediate 8 (2.4 g) in acetic anhydride (30 ml) was heated at 100° for 0.5 h and then cooled. The reaction mixture was stored at 5° for 2 h and the solid collected by filtration, washed with acetic anhydride, ethyl acetate and ether, and dried (0.1 mm at 80°) to yield the title compound (2.244 g) m.p. 207°–210° (decomp.) $\lambda_{max}$ 243 nm, $E_1^1$ 945, 373 nm, $E_1^1$ 142.

Intermediate 10

5,8,13,14-Tetrahydro-9- and 12-hydroxy-14-methylbenz[5,6]-isoindolo[2,1-b]-isoquinoline-8,13-dione Acetic anhydride (160 ml) was added to a mixture of N-formyl-1,2,3,4-tetrahydroisoquinoline-4-methyl-3-carboxylic acid (20 g) and 5-hydroxy-1,4-napthoquinone (31.78 g). The reaction mixture was heated at 100° for ½ h and was then left to cool overnight (16 h) followed by further cooling for 1 h. A precipitate formed which was filtered, and was shown by thin layer chromatography to be a mixture of 9-hydroxy and 12-hydroxy isomers. The isomers were separated by chromatography on silica gel (using dichloromethane as solvent). From the early fractions the 9-hydroxy isomer, which was the minor component, was obtained. The major component, the the 12-hydroxy isomer of the title compound was collected from late fractions, $\lambda_{max}$ 243 nm, $E_1^1$ 1103, 397 nm, $E_1^1$ 381.

Intermediate 11

Chloroacetic acid [5,8,13,14-tetrahydro-14-methyl-8,13-dioxobenz[5,6]-isoindolo[2,1-b]isoquinolin-12-yl]ester Sodium hydride (60% dispersion) was washed with petroleum ether (b.p. 40°–60°) under nitrogen, tetrahydrofuran (10 ml) was added followed by the 12-hydroxy isomer of Intermediate 10 (0.5 g) dissolved in tetrahydrofuran (10 ml). The reaction mixture was stirred for 10 min and chloroacetyl chloride (0.15 ml) was added. The mixture was then stirred for a further 10 min. 2-Propanol (1 ml) was added followed by a small quantity of water, which was added dropwise. The mixture was poured onto ice and extracted with ethyl acetate (×3). Crystallisation occurred on evaporation to low volume to yield the title compound (168 mg) m.p. 218°–220° (d).

Intermediate 12

Iodoacetic acid, [5,8,13,14-tetrahydro-14-methyl-8,13-dioxobenz[5,6]-isoindolo[2,1-b]isoquinolin-12-yl]ester Intermediate 11 (2.45 g) was dissolved in acetone (200 ml) and sodium iodide (6 g) was added. The reaction mixture was stirred for 18 h at room temperature then evaporated to dryness and redissolved in chloroform. The inorganic material has removed by filtration, and the solution was then evaporated to dryness. Crystallisaton from dichloromethane-petroleum ether (bp 40°–60°) yielded the title compound m.p. 205°–210° (d).

Product Example

Example 1

(Diethylamino)acetic acid, [5,8,13,14-tetrahydro-8,13-dioxobenz-[5,6]isoindolo[2,1-b]isoquinoline-9,12-diyl]ester Intermediate 6 (1.656 g) and diethylamine (0.5 ml) in acetone (165 ml) were stirred at room temperature for 15 minutes. Further diethylamine (0.5 ml) was added and the miture was stirred for 35 minutes then acidified with 4N hydrochloric acid and water added. The solution was extracted with dichloromethane and the organic layer was discarded. The solution was then made alkaline with aqueous saturated sodium bicarbonate and extracted with dichloromethane (3×) to yield the title compound (1.2 g). Crystallisation from ether gave the title compound (670 mg) m.p. 125°–130°; $\lambda_{max}$ (ethanol) 243 ($E_1^1$ 646) and 385 nm ($E_1^1$ 110); $\delta$(CDCl$_3$) (1.2, 1.16) CH$_3$, (2.84, 2.8) CH$_2$, (3.87, 3.8) OCH$_2$.

Example 2

(Diethylamino)acetic acid, [5,8,13,14-tetrahydro-8,13-dioxobenz[5,6]-isoindolo[2,1-b]isoquinoline-9,12-diyl]ester, dihydrochloride The compound of Example 1 (600 mg) was dissolved in water (60 ml) containing N-hydrochloric acid (2.28 ml) and the solution was freeze-dried to yield the title compound (740 mg) $\lambda_{max}$ (water) 246 ($E_1^1$450) and 406.5 nm ($E_1^1$ 91).

Example 3

(Diethylamino)acetic acid, [5,8,13,14-tetrahydro-8,13-dioxobenz[5,6]-isoindolo[2,1-b]isoquinolin-9-yl]ester Intermediate 3 (5.2 g) and diethylamine (5 ml) in acetone (1250 ml) were stirred at room temperature for 135 minutes, then filtered, evaporated and triturated with acetone to give the title compound (2.1 g). A sample was recrystallised from acetone-petroleum ether b.p. 60°–80° to give the title compound m.p. 190°–192°; $\lambda_{max}$(ethanol) 243.5 ($E_1^1$ 1071) and 385 nm ($E_1^1$ 177); $\delta$(CDCl$_3$) 1.17 (CH$_3$, ethyl), 2.84 (CH$_2$), 3.85 (OCH$_2$).

Example 4

(Diethylamino)acetic acid, [5,8,13,14-tetrahydro-8,13-dioxobenz[5,6]-isoindolo[2,1-b]isoquinolin-9-yl]ester, hydrochloride The compound of Example 3 (1.875 g) was suspended in water (562 ml) and N-hydrochloric acid (4.38 ml) was added. The mixture was stirred for 15 minutes and further N-hydrochloric acid (4.38 ml) was added. After stirring for a further 15 minutes the pH was adjusted to 3 and the solution was filtered and freeze-dried to yield the title compound (2.33 g) $\lambda_{max}$ (water) 245 ($E_1^1$ 577) and 393.5 nm ($E_1^1$ 95).

Example 5

(Dipropylamino)acetic acid, [5,8,13,14-tetrahydro-8,13-dioxobenz[5,6]-isoindolo[2,1-b]isoquinolin-9-yl]ester Intermediate 3 (3 g) and dipropylamine (6 ml) in acetone (900 ml) were stirred at 40°–45° for 30 minutes. The solvent was reduced to a low volume and the crude title compound (2.3 g) was collected by filtration. Recrystallisation from acetone gave the title compound (1.5 g) m.p. 199°–201°, $\lambda_{max}$(ethanol) 243.5 ($E_1^1$904) and 376 nm ($E_1^1$143), $\delta$(CDCl$_3$) 0.94 (CH$_3$), 1.7–1.5 (CH$_2$), 2.71 (CH$_2$).

Example 6

(Dipropylamino)acetic acid, [5,8,13,14-tetrahydro-8,13-dioxobenz[5,6]-isoindolo[2,1-b]isoquinolin-9-yl]ester, hydrochloride The compound of Example 5 (442 mg) in water (200 ml) containing N-hydrochloric acid (4 ml) was stirred for 90 minutes after which further N-hydrochloric acid (2 ml) was added. When solution occured, the pH was adjusted to 3, filtered and freeze-dried to give the title compound (682 mg) $\lambda_{max}$ (water) 245.5 nm ($E_1^1$ 293).

Example 7

(Diethylamino)acetic acid, [5,8,13,14-tetrahydro-14-methyl-8,13-dioxobenz[5,6]isoindolo[2,1-b]isoquinolin-9-yl]ester A mixture of Intermediate 9 (2 gram) and diethylamine (1 ml) in acetone (200 ml) was stirred at 20° for 0.5 h, filtered and the filtrate evaporated to dryness and dried (0.1 mm overnight). The solid was dissolved in acetone by heating, the solution was filtered, evaporated to low volume and then allowed to stand at room temperature for 1 h. The resulting precipitated solid was collected by filtration, washed with a small amount of acetone and dried at 100° (0.1 mm) to yield the title compound (1.18 g) m.p. 191°–192°; $\lambda_{max}$ 243 nm ($E_1^1$ 974), 390 nm ($E_1^1$ 135); $\delta$(CDCl$_3$) 1.53 (CH$_3$), 1.18 (CH$_3$, ethyl), 2.87 (CH$_2$, ethyl), 3.85 (OCH$_2$).

Example 8

(Diethylamino)acetic acid, [5,8,13,14-tetrahydro-14-methyl-8,13-dioxobenz[5,6]isoindolo[2,1-b]isoquinolin-9-yl]ester, hydrochloride A mixture of the compound of Example 7 (1.1 g), N-hydrochloric acid (5 ml) and water (160 ml) was stirred at 20° for 5 mins. Solution was obtained almost immediately. The pH was adjusted to 3 with an approximately 1 molar equivalent of N NaOH. The solution was filtered and freeze-dried and then dried (CaCl$_2$, 0.1 mm, 24 h) to yield the title compound (1.23 g) $\lambda_{max}$ 245 nm ($E_1^1$418) 389, ($E_1^1$ 63).

Example 9

(Dimethylamino)acetic acid, [5,8,13,14-tetrahydro-14-methyl-8,13-dioxobenz[5,6]isoindolo[2,1-b]-isoquinolin-9-yl]ester To a suspension of Intermediate 9 (1.5 g) in acetone (120 ml) was added a solution of dimethylamine in acetone (6.45M, 0.9 ml). The reaction mixture was stirred at 20° for 2 h, then filtered and evaporated to dryness to yield a yellow solid which was dried overnight in vacuo. The solid was dissolved in dichloromethane and extracted into 2N hydrochloric acid. An emulsion formed and was dispersed with a large volume of water. The aqueous layer was basified (10% NaOH) and back extracted into dichloromethane. The organic solution was dried (Na$_2$SO$_4$) and evaporated to dryness, giving the title compound (108 mg) $\lambda_{max}$ 242.6 nm, $E_1^1$=861, $\delta$(CDCl$_3$) 1.55 (CH$_3$), 2.54 [N—(CH$_3$)$_2$], 3.69 (COCH$_2$N), 4.94 (CH) 5.22–5.12 (CH$_2$).

Example 10

(Diethylamino) acetic acid, [5,8,13,14-tetrahydro-14-methyl-8,13-dioxo-benz[5,6]isoindolo[2,1-b]isoquinolin-12-yl]ester Intermediate 12 (1 g) and diethylamine (0.42 ml) in acetone (100 ml) was stirred at room temperature for 15 min. The resulting solution was then evaporated to dryness under reduced pressure to give an oil which on mixture with ethyl acetate gave a solid which was washed with water and dried. Crystallisation from methyl acetate gave the title compound (410 mg) m.p. 190°–193°. $\lambda_{max}$ 243 nm, $E_1^1$981, $\delta$ (CDCl$_3$) 1.50 (14-CH$_3$) 3.97, 4.07 (CH$_2$ of ester) 1.33 (CH$_3$ of ethyl), 2.99 (CH$_2$ of ethyl).

Example 11

(Diethylamino)acetic acid [5,8,13,14-tetrahydro-14-methyl-8,13-dioxobenz[5,6]isoindolo[2,1-b]isoquinolin-12-yl]ester, hydrochloride The compound of Example 10 (375 mg). 0.1N hydrochloric acid (20 ml) and water (375 ml) was stirred at room temperature for 30 min, filtered, and freeze-dried to yield the title compound (40 mg) λmax 244 nm, $E_1^1$ 481 δ (CDCl$_3$) 1.58 (14-Me) 4.71 (CH$_2$ of ester) 1.71 (CH$_3$ of ethyl) 3.78 (CH$_2$ of ethyl).

Example 12

Suspension for parenteral administration "Active ingredient" as used in the following may be for example the compound of Example 7.

| Active ingredient | 1000 mg |
|---|---|
| Tween 80 | 1000 mg |
| Dimethylformamide | 1000 ml |
| Fresh distilled water | 1000 ml |
| Replacement Vehicle | |
| Tween 80 | 50 mg |
| Sodium chloride | 900 mg |
| Fresh distilled water to | 100 ml |

Method of preparation

Dissolve tween 80 (100 mg) and the active ingredient (100 mg) in the dimethylformamide. Add this solution to the fresh distilled water (100 ml) using a radial Silverson fitted with an injection tube. Stir for 30 minutes. Pour the suspension into centrifuge tubes and centrifuge at 300 rpm until the supernatant is clear. Decant the supernatant. Resuspend the "cake" with a portion of the replacement vehicle. Make up to 100 ml with replacement vehicle.

We claim:

1. A compound having a formula (1)

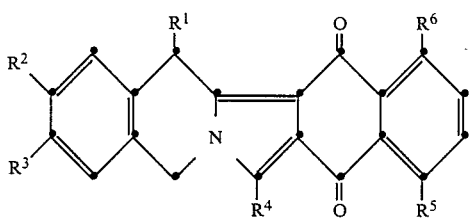

wherein
$R^1$ is a methyl group;
$R^2$ is a hydrogen atom or a hydroxyl, $C_{1-4}$ alkoxy or $C_{2-4}$ alkanoyloxy group;
$R^3$ is a hydrogen atom, or when $R^2$ is other than a hydrogen atom, optionally a hydroxyl, $C_{1-4}$ alkoxy or $C_{2-4}$ alkanoyloxy group, or
$R^2$ and $R^3$ together are a methylenedioxy group;
$R^4$ is a hydrogen or halogen atom or a methyl group;
$R^5$ is a group —OCOCH$_2$NR$^7$R$^8$ where $R^7$ and $R^8$, which may be the same or different, each is a hydrogen atom or a straight or branched $C_{1-4}$ alkyl group optionally substituted by a hydroxyl group;
$R^6$ is a hydrogen atom; and physiologically acceptable salts thereof.

2. A compound of formula (1) as claimed in claim 1 wherein $R^5$ is a group of formula —OCOCH$_2$NR$^7$R$^8$ wherein $R^7$ and $R^8$ are straight or branched $C_{1-4}$ alkyl groups; and physiologically acceptable salts thereof.

3. A compound of formula (1) as claimed in claim 1 wherein $R^2$ and $R^3$ are hydrogen atoms and $R^4$ is a hydrogen or bromine atom or a methyl group; and physiologically acceptable salts thereof.

4. A compound of formula (1) as claimed in claim 2 wherein $R^2$ and $R^3$ are hydrogen atoms and $R^4$ is a hydrogen or bromine atom or a methyl group; and physiologically acceptable salts thereof.

5. A compound as claimed in claim 1 being compounds of formula (1a)

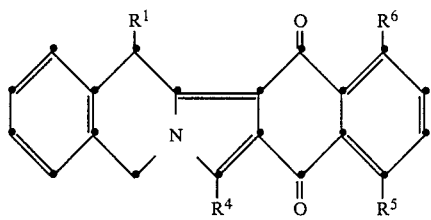

wherein
$R^1$ is a methyl group;
$R^4$ is a hydrogen or halogen atom or a methyl group;
$R^5$ is a group —OCOCH$_2$NR$^7$R$^8$ where $R^7$ and $R^8$, which may be the same or different, each is a straight or branched $C_{1-4}$ alkyl group;
$R^6$ is a hydrogen atom; and physiologically acceptable salts thereof.

6. A compound of formula (1a) as claimed in claim 5 wherein $R^1$ is a methyl group, $R^4$ is a hydrogen or bromine atom or a methyl group, $R^5$ is a group of formula —OCOCH$_2$NR$^7$R$^8$, $R^6$ is a hydrogen atom and $R^7$ and $R^8$ are straight or branched $C_{1-4}$ alkyl groups; and physiologically acceptable salts thereof.

7. A compound as claimed in claim 1 being [5,8,13,14-tetrahydro-14-methyl-8,13-dioxobenz[5,6]-isoindolo[2,1-b]isoquinolin-9-yl](diethylamino)acetate or a physiologically acceptable salt thereof.

8. A pharmaceutical composition comprising a compound of formula (1) as defined in claim 1, or a physiologically acceptable salt thereof, together with at least one pharmaceutical carrier or excipient.

9. A compound of formula (2)

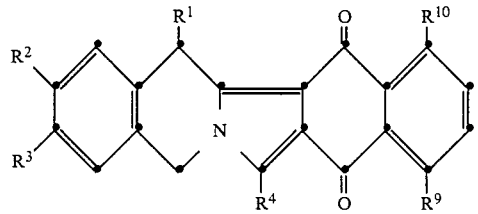

wherein $R^4$ is a hydrogen atom or a methyl group; $R^9$ is a group —OCOCH$_2$L in which L is a halogen atom or a hydrocarbylsulphonyloxy group; $R^{10}$ is a hydrogen atom; $R^1$ is a methyl group; $R^2$ is a protected hydroxyl group or is a hydrogen atom, hydroxyl, $C_{1-4}$ alkoxy or $C_{2-4}$ alkanoyloxy group; and $R^3$ is a protected hydroxyl group or is a hydrogen atom, or (when $R^2$ is other than hydrogen) optionally a hydroxyl, $C_{2-4}$ alkoxy or $C_{2-4}$ alkanoyloxy group or $R^2$ and $R^3$ together are a methylenedioxy group.

* * * * *